United States Patent [19]

Hutt, Jr.

[11] Patent Number: 4,473,568

[45] Date of Patent: Sep. 25, 1984

[54] ANTIBACTERIAL THIAZOLIDINE OR THIOMORPHOLINE SUBSTITUTED QUINOLINES

[75] Inventor: Marland P. Hutt, Jr., Saline, Mich.

[73] Assignee: Warner Lambert Company, Morris Plains, N.J.

[21] Appl. No.: 471,080

[22] Filed: Mar. 1, 1983

[51] Int. Cl.[3] .................... A01N 43/78; A01N 43/84; C07D 417/02
[52] U.S. Cl. ............................... 424/246; 424/248.51; 424/258; 544/58.2; 544/58.6; 544/101; 546/156
[58] Field of Search .................... 544/58.2, 58.6, 101; 546/156; 424/246, 248.51, 258

[56] References Cited

U.S. PATENT DOCUMENTS

| | | | |
|---|---|---|---|
| 4,292,317 | 9/1981 | Pesson | 546/156 X |
| 4,382,892 | 5/1983 | Hayakawa et al. | 544/101 X |
| 4,398,029 | 8/1983 | Irikura et al. | 546/156 X |
| 4,399,134 | 8/1983 | Ishikawa et al. | 544/58.2 X |

FOREIGN PATENT DOCUMENTS 57-149286  9/1982  Japan .

Primary Examiner—Richard L. Raymond
Attorney, Agent, or Firm—Ronald A. Daignault

[57] ABSTRACT

Certain thiazolidine or thiomorpholine substituted quinoline and pyridobenzoxazine compounds are antibacterial agents. Method for their preparation and use are disclosed.

10 Claims, No Drawings

ANTIBACTERIAL THIAZOLIDINE OR THIOMORPHOLINE SUBSTITUTED QUINOLINES

BACKGROUND OF THE INVENTION

The Journal of Medicinal Chemistry, 23, 1358 (1980) discloses certain substituted quinoline-3-carboxylic acids having the structural formula

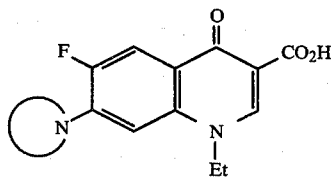

wherein N- may be pyrrolidinyl, piperidinyl or morpholino. See also U.S. Pat. No. 4,146,719. The compounds are disclosed to have antibacterial activity.

Similar compounds having similar activity are disclosed in Belgian Pat. No. 884,824 and have the formula

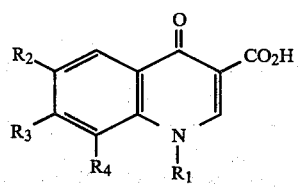

wherein $R_1$ is lower alkyl; $R_2$ is halogen; $R_3$ is piperazinyl or N-lower alkyl piperazinyl; $R_4$ is halogen or lower alkyl; or $R_1$ and $R_4$ are alkyl and together complete a hexagonal ring which may be substituted by lower alkyl.

British Patent Specification No. 2,093,018 published Aug. 25, 1982, discloses compounds as above where substituted amines include morpholine.

European patent application No. 81 10 6747, published Mar. 10, 1982, discloses certain benzoxazine derivatives having the structural formula

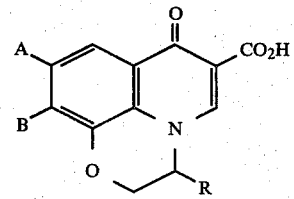

wherein A is halogen and B may be a cyclic amine substituent such as pyrrolidine, or piperidine. The compounds are disclosed to have antibacterial activity.

Belgian Pat. No. 891,046 published Mar. 1, 1982, discloses compound of the formula

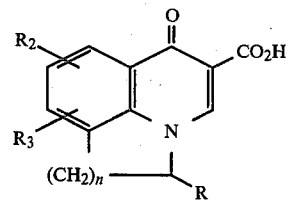

as antibacterials, the cyclic amine $R_3$ substitutent includes piperazino, morpholino, and thiomorpholino.

SUMMARY OF THE INVENTION

The invention sought to be patented in a first generic chemical compound aspect is a compound having the structural formula Ia or Ib

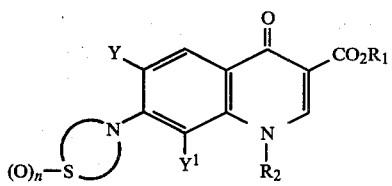

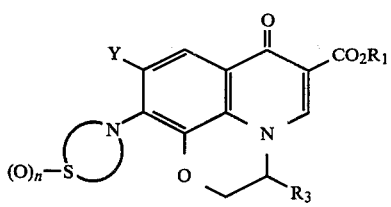

wherein
Y and $Y^1$ are independently hydrogen, fluorine, chlorine, or bromine;
n is 0 or the integer 1 or 2;
$R_1$ is hydrogen, alkyl having from one to six carbon atoms or a cation derived from a pharmaceutically acceptable metal or amine;
$R_2$ is alkyl having from one to four carbon atoms, vinyl or haloalkyl having from two to four carbon atoms;
$R_3$ is hydrogen, methyl, or ethyl;

is thiazolidine or thiomorpholine;
and the pharmaceutically acceptable salts thereof.

The invention sought to be patented in a first subgeneric aspect of its first chemical compound aspect is a compound having the structural formula Ia defined above, and the pharmaceutically acceptable salts thereof.

The invention sought to be patented in a second subgeneric aspect of its first chemical compound aspect is a compound having the structural formula Ib defined above, and the pharmaceutically acceptable salts thereof.

The invention sought to be patented in a third subgeneric aspect of its first chemical compound aspect is a compound having the structural formula Ia or Ib wherein Y is fluorine; $Y^1$ is hydrogen or fluorine; $R_2$ is ethyl; $R_3$ is methyl, and the pharmaceutically acceptable salts thereof.

The invention sought to be patented as species of its first generic chemical compound aspect are the compounds having the names:

1-ethyl-6-fluoro-1,4-dihydro-4-oxo-b 7-(3-thiazolidinyl)-3-quinolinecarboxylic acid;

1-ethyl-6-fluoro-1,4-dihydroxy-4-oxo-7-(4-thiomorpholinyl)-3-quinolinecarboxylic acid;

1-ethyl-6-fluoro-1,4-dihydro-4-oxo-7-(4-thiomorpholinyl)-3-quinolinecarboxylic acid, S-oxide;

1-ethyl-6-fluoro-1,4-dihydro-4-oxo-7-(4-thiomorpholinyl)-3-quinolinecarboxylic acid, S,S-dioxide;

1-ethyl-6,8-difluoro-1,4-dihydro-4-oxo-7-(3-thiazolidinyl)-3-quinolinecarboxylic acid;

1-ethyl-6,8-difluoro-1,4-dihydro-4-oxo-7-(4-thiomorpholinyl)-3-quinolinecarboxylic acid;

3-methyl-9-fluoro-10-(3-thiazolidinyl)-2,3-dihydro-7-oxo-7H-pyrido-[1,2,3-de]-1,4-benzoxazine-6-carboxylic acid; and 3-methyl-9-fluoro-10-(4-thiomorpholine)-2,3-dihydro-7-oxo-7H-pyrido-[1,2,3-de]-1,4-benzoxazine-6-carboxylic acid; and the pharmaceutically acceptable salts thereof.

The invention sought to be patented in its chemical process aspect is a process for preparing a compound having the structural formula Ia or Ib as defined hereinabove which comprises reacting a compound having the structural formula IIIa or IIIb

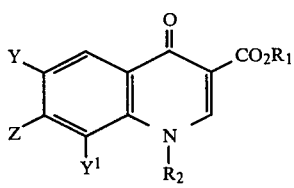

IIIa

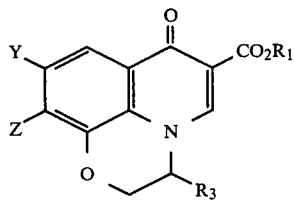

IIIb with a compound having the structural formula II

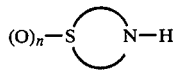

and, when n is 0, oxidizing if desired the resulting compound to a compound of the formula Ia or Ib wherein n is 1 or 2; wherein X, Y, Y$^1$, R$_1$–R$_3$ are defined hereinabove and Z is fluorine or chlorine.

The invention sought to be patented in its pharmaceutical composition aspect is a pharmaceutical composition which comprises a compound having structural formula Ia or Ib and the pharmaceutically acceptable salts thereof in combination with a pharmaceutically acceptable carrier.

The invention sought to be patented in its pharmaceutical method aspect is a method for treating bacterial infections in a mammal which comprises administering an antibacterial effective amount of the above defined pharmaceutical composition to a mammal in need thereof.

DESCRIPTION OF THE PREFERRED EMBODIMENTS

The compounds of the invention having the structural formula Ia or Ib may be readily prepared by treating a corresponding compound having the structural formula IIIa or IIIb with the desired cyclic amine, II.

The reaction between the compound of structural formula IIIa or IIIb and a compound of formula II may be performed with or without a solvent, preferably at elevated temperature for a sufficient time so that the reaction is substantially complete. The reaction is preferably carried out in the presence of an acid acceptor such as an alkali metal or alkaline earth metal carbonate or bicarbonate, a tertiary amine such as triethylamine, pyridine, or picoline. Alternatively an excess of the compound of formula II may be utilized as the acid acceptor.

Convenient solvents for this reaction are non-reactive solvents such as acetonitrile, tetrahydrofuran, ethanol, chloroform, dimethylsulfoxide, dimethylformamide, pyridine, picoline, water, and the like. Solvent mixtures may also be utilized.

Convenient reaction temperatures are in the range of from about 20° to about 150° C.; higher temperatures usually require shorter reaction times.

The compounds of the invention having the structural formula Ia or Ib and n is 1 or 2 can be prepared conveniently from the same compounds where n is 0 by an oxidation reaction. For example, the compounds where n is 1 are prepared by oxidation of the compounds where n is 0 with the bromine complex of 1,4-diazabicyclo[2.2.2.]octane at or near room temperature. The compounds of the formula Ia or Ib where n is 2 may be prepared directly from the corresponding n=0 compounds by treatment with 30% hydrogen peroxide at or near room temperature.

The starting compounds having structural formulae IIIa and IIIb are known in the art. Thus the following compounds are disclosed in the noted references:

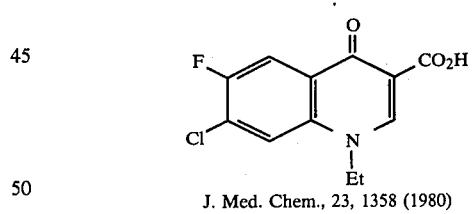

J. Med. Chem., 23, 1358 (1980)

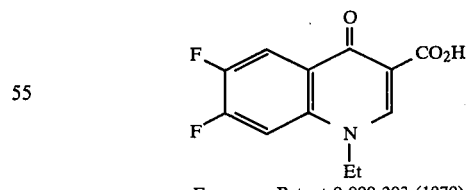

European Patent 0 000 203 (1979)

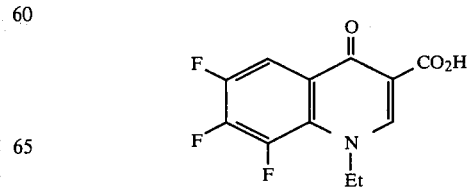

British Patent 2,057,440

-continued

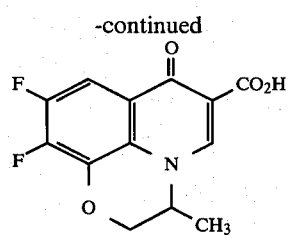

European Patent Application 81 10 6747

The compounds of the invention having structural formula II, where n=0, are commercially available.

The compounds of the invention having structural formulae Ia and Ib display antibacterial activity when tested by the microtitration dilution method as described in Heifetz, et al, Antimicr. Agents & Chemoth., 6, 124 (1974), which is incorporated herein by reference.

By use of the above referenced method, the following minimum inhibitory concentration values (MIC's in μg/ml) were obtained for representative compounds of the invention.

IN VITRO ANTIBACTERIAL ACTIVITY
Minimal Inhibitory Concentration
MIC (μg/ml)

| Organisms | Ex. 1 Compound | Ex. 2 Compound | Ex. 3 Compound | Ex. 4 Compound | Ex. 5 Compound | Ex. 6 Compound |
|---|---|---|---|---|---|---|
| Enterobacter cloacae MA 2646 | 0.4 | 0.4 | 0.8 | 0.4 | 0.4 | <0.1 |
| Escherichia coli Vogel | 0.05 | 0.1 | 0.8 | <0.1 | <0.1 | <0.1 |
| Klebsiella pneumoniae MGH-2 | 0.4 | 0.2 | 3.1 | <0.1 | 0.4 | 0.2 |
| Proteus rettgeri M 1771 | 0.2 | 0.4 | 1.6 | 0.2 | 0.4 | 0.4 |
| Pseudomonas aeruginosa UI-18 | 3.1 | 0.8 | 0.8 | 0.2 | 0.4 | 1.6 |
| Staphylococcus aureus H 228 | 0.013 | 0.006 | 1.6 | 0.4 | <0.1 | <0.1 |
| Staphylococcus aureus UC-76 | 0.006 | 0.006 | <0.1 | <0.1 | <0.1 | <0.1 |
| Streptococcus faecalis MGH-2 | 0.4 | 0.4 | 1.6 | 0.8 | 0.2 | <0.1 |
| Streptococcus pneumoniae SV-1 | 6.3 | 12.5 | 50 | 12.5 | 1.6 | 0.2 |
| Streptococcus pyogenes C-203 | 12.5 | 6.3 | 25 | 6.3 | 0.8 | 0.2 |

The compounds of the invention having the structural formulae Ia and Ib form pharmaceutically acceptable salts with pharmaceutically acceptable organic and inorganic acids. Examples of suitable acids for salt formation are hydrochloric, sulfuric, phosphoric, acetic, citric, oxalic, malonic, salicylic, malic, gluconic, fumaric, succinic, ascorbic, maleic, methanesulfonic, and the like. The salts are prepared by contacting the free base form with a sufficient amount of the desired acid to produce either a mono or di salt in the conventional manner. The free base forms may be regenerated by treating the salt form with a base. For example, dilute aqueous base solutions may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention.

The compounds of the invention can exist in unsolvated as well as solvated forms, including hydrated forms. In general, the solvated forms, with pharmaceutically acceptable solvents such as water, ethanol, and the like are equivalent to the unsolvated forms for purposes of the invention.

The alkyl groups contemplated by the invention comprise both straight and branched carbon chains of from one to about six carbon atoms unless otherwise specified. Representative of such groups are methyl, ethyl, propyl, isopropyl, butyl, t-butyl, 2-methylpentyl, and the like.

The term, haloalkyl, is intended to include halogen substituted straight and branched carbon chains of from two to four carbon atoms. Those skilled in the art will recognize that the halogen substituent may not be present on the α-carbon atom of the chain. Representative of such groups are β-fluoroethyl, β-chloroethyl, β,β-dichloroethyl, β-chloropropyl, β-chloro-2-propyl, β-iodobutyl, and the like.

The term halogen is intended to include fluorine, chlorine, bromine, and iodine unless otherwise specified.

The compounds of formula Ib contain an asymmetric carbon atom. The pure D isomer, pure L isomer as well as mixtures thereof, including the racemic mixtures, are contemplated by the invention.

The compounds of the invention can be prepared and administered in a wide variety of oral and parenteral dosage forms. It will be obvious to those skilled in the art that the following dosage forms may comprise as the active component, either a compound of formula Ia or Ib or a corresponding pharmaceutically acceptable salt of a compound of formula Ia or Ib, or a mixture of such compounds and/or salts.

For preparing pharmaceutical compositions from the compounds described by this invention, inert, pharmaceutically acceptable carriers can be either solid or liquid. Solid form preparations include powders, tablets, dispersable granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

Liquid form preparations include solutions suspensions and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspensions suitable for oral use can be made by dispersing the finely divided active component in water with viscous material, i.e., natural or synthetic gums, resins, methyl cellulose, sodium carboxymethyl cellulose, and other well-known suspending agents.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules and powders in vials or ampoules. The unit dosage form can also be a capsule, cachet, vial, ampoule, or tablet itself or it can be the appropriate number of any of these packaged forms.

The quantity of active compound in a unit dose of preparation may be varied or adjusted from 1 mg to 100 mg according to the particular application and the potency of the active ingredient.

In therapeutic use as agents for treating bacterial infections the compounds of structural formula Ia and Ib utilized in the pharmaceutical method of this invention are administered at the initial dosage of about 200 mg to about 2400 mg daily. A daily dose range of about 400 mg to about 800 mg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventors' preferred methods for preparing the compounds of the invention.

EXAMPLE 1

1-Ethyl-6-fluoro-1,4-dihydro-4-oxo-7-(3-thiazolidinyl)-3-quinolinecarboxylic acid A solution of 1.01 g (4.0 mmol) of 1-ethyl-6,7-difluoro-1,4-dihydro-4-oxo-3-quinolinecarboxylic acid, 0.79 ml (10 mmol) of thiazolidine, 20 ml of acetonitrile and 20 ml of N,N-dimethylformamide was heated at reflux for 16 hours. The reaction was cooled to room temperature and the solid which formed was removed by filtration. After triturating with hot methanol, the residue was recrystallized from N,N-dimethylformamide to give 0.13 g of 1-ethyl-6-fluoro-1,4-dihydro-4-oxo-7-(3-thiazolidinyl)-3-quinolinecarboxylic acid; mp 270°–273° C.

EXAMPLE 2

1-Ethyl-6-fluoro-1,4-dihydro-4-oxo-7-(4-thiomorpholinyl)-3-quinolinecarboxylic acid A solution of 1.35 g (5.33 mmol) of 1-ethyl-6,7-difluoro-1,4-dihydro-4-oxo-3-quinolinecarboxylic acid, 1.34 ml (13.3 mmol) of thiomorpholine, 40 ml of acetonitrile, and 20 ml of N,N-dimethylformamide was heated under reflux for 21 hours. The reaction mixture was cooled to room temperature and the solid was collected by filtration, washed with water and acetonitrile, and dried to give 1.18 g of 1-ethyl-6-fluoro-1,4-dihydro-4-oxo-7-(4-thiomorpholinyl)-3-quinolinecarboxylic acid, mp 254°–6°.

EXAMPLE 3

1-Ethyl-6-fluoro-1,4-dihydro-4-oxo-7-(4-thiomorpholinyl)-3-quinolinecarboxylic acid, S-oxide A suspension of 0.34 g (1.0 mmol) of 1-ethyl-6-fluoro-1,4-dihydro-4-oxo-7-(4-thiomorpholinyl)-3-quinolinecarboxylic acid, 0.43 g (1.0 mmol) of the bromine complex of 1,4-diazabicyclo [2.2.2.] octane and 20 ml of 70% acetic acid was stirred at room temperature for four days. The reaction mixture was diluted to 100 ml with water and the solid was collected by filtration to give 0.12 g of 1-ethyl-6-fluoro-1,4-dihydro-4-oxo-7-(4-thiomorpholinyl)-3-quinolinecarboxylic acid, S-oxide, mp 284° dec.

EXAMPLE 4

1-Ethyl-6-fluoro-1,4-dihydro-4-oxo-7-(4-thiomorpholinyl)-3-quinolinecarboxylic acid, S,S-dioxide A suspension of 0.34 g (1.0 mmol) of 1-ethyl-6-fluoro-1,4-dihydro-4-oxo-7-(4-thiomorpholinyl)-3-quinolinecarboxylic acid, 1.0 ml (10 mmol) of 30% hydrogen peroxide, and 20 ml of 70% acetic acid was stirred at room temperature for 21 hours. The reaction mixture was diluted with water and the solid was collected by filtration to give 0.30 g of 1-ethyl-6-fluoro-1,4-dihydro-4-oxo-7-(4-thiomorpholinyl)-3-quinolinecarboxylic acid, S,S-dioxide, mp 300°–5° dec.

EXAMPLE 5

1-Ethyl-6,8-difluoro-1,4-dihydro-4-oxo-7-(4-thiomorpholinyl)-3-quinolinecarboxylic acid A solution of 0.54 g (2.0 mmol) 1-ethyl-6,7,8-trifluoro-1,4-dihydro-4-oxo-3-quinolinecarboxylic acid, 0.50 ml (5.0 mmol) thiomorpholine, and 20 ml of acetonitrile was heated under reflux for 17 hours. The reaction mixture was cooled and the solid was collected by filtration and washed with acetonitrile and ether to give 0.44 g of 1-ethyl-6,8-difluoro-1,4-dihydro-4-oxo-7-(4-thiomorpholinyl)-3-quinolinecarboxylic acid, mp>300°.

EXAMPLE 6

9-Fluoro-2,3-dihydro-3-methyl-7-oxo-10-(4-thiomorpholinyl)-7H-pyrido[1,2,3-de]-1,4-benzoxazine-6-carboxylic acid A mixture of 0.18 g (0.6 mmol) of 9,10-difluoro-2,3-dihydro-3-methyl-7-oxo-7H-pyrido[1,2,3-de]-1,4-benzoxazine-6-carboxylic acid, 0.3 ml (3.0 mmol) of thiomorpholine and 20 ml of pyridine was heated under reflux for 21 hours. The solution was evaporated to dryness, the residue was triturated with hot methanol, and filtered to give 0.05 g of the title compound, mp>300°.

I claim:

1. A compound having the structural formula Ia

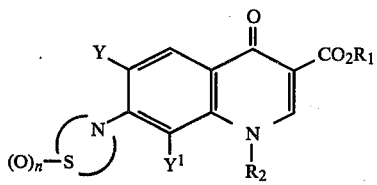

wherein

Y and $Y^1$ are independently hydrogen, fluorine, chlorine, or bromine;

n is 0 or the integer 1 or 2;

$R_1$ is hydrogen, alkyl having from one to six carbon atoms or a cation derived from a pharmaceutically acceptable metal or amine;

$R_2$ is alkyl having from one to four carbon atoms, vinyl or haloalkyl having from two to four carbon atoms;

$R_3$ is hydrogen, methyl, or ethyl;

is thiazolidine or thiomorpholine;

and the pharmaceutically acceptable salts thereof.

2. A compound defined in claim 1 wherein Y is fluorine; Y' is hydrogen or fluorine; $R_2$ is ethyl; $R_3$ is methyl, and the pharmaceutically acceptable salts thereof.

3. The compound defined in claim 1 having the name 1-ethyl-6-fluoro-1,4-dihydro-4-oxo-7-(3-thiazolidinyl)-3-quinolinecarboxylic acid and the pharmaceutically acceptable salts thereof.

4. The compound defined in claim 1 having the name 1-ethyl-6-fluoro-1,4-dihydro-4-oxo-7-(4-thiomorpholinyl)-3-quinolinecarboxylic acid and the pharmaceutically acceptable salts thereof.

5. The compound defined in claim 1 having the name 1-ethyl-6-fluoro-1,4-dihydro-4-oxo-7-(4-thiomorpholinyl)-3-quinolinecarboxylic acid, S-oxide and the pharmaceutically acceptable salts thereof.

6. The compound defined in claim 1 having the name 1-ethyl-6-fluoro-1,4-dihydro-4-oxo-7-(4-thiomorpholinyl)-3-quinolinecarboxylic acid, S,S-dioxide and the pharmaceutically acceptable salts thereof.

7. The compound defined in claim 1 having the name 1-ethyl-6,8-difluoro-1,4-dihydro-4-oxo-7-(3-thiazolidinyl)-3-quinolinecarboxylic acid and the pharmaceutically acceptable salts thereof.

8. The compound defined in claim 1 having the name 1-ethyl-6,8-difluoro-1,4-dihydro-4-oxo-7-(4-thiomorpholinyl)-3-quinolinecarboxylic acid and the pharmaceutically acceptable salts thereof.

9. A pharmaceutical composition which comprises an antibacterially effective amount of a compound as defined in claim 1, in combination with a pharmaceutically acceptable carrier.

10. A method for treating bacterial infections in a mammal which comprises administering an antibacterial effective amount of the pharmaceutical composition defined in claim 9 to a mammal in need thereof.

* * * * *